(12) United States Patent
Robinson et al.

(10) Patent No.: US 6,409,698 B1
(45) Date of Patent: Jun. 25, 2002

(54) PERFORATE ELECTRODIFFUSION PUMP

(75) Inventors: John N. Robinson, 2165 Chardonnay Cir., Gibsonia, PA (US) 15044; Paul F. Burke, Bellingham; Kenneth A. Fine, Sharon, both of MA (US)

(73) Assignee: John N. Robinson, Gibsonia, PA (US)

( * ) Notice: Subject to any disclaimer, the term of this patent is extended or adjusted under 35 U.S.C. 154(b) by 64 days.

(21) Appl. No.: 09/723,057

(22) Filed: Nov. 27, 2000

(51) Int. Cl.$^7$ .......................... R01D 57/02; A61N 1/30
(52) U.S. Cl. .................. 604/19; 417/48; 435/173.6; 604/501; 204/550
(58) Field of Search .................. 435/173.6; 604/20, 604/19, 501; 417/48; 2204/550, 518

(56) References Cited

U.S. PATENT DOCUMENTS

| | | | |
|---|---|---|---|
| 3,427,978 A | * 2/1969 | Hanneman et al. | 417/48 |
| 3,923,426 A | * 12/1975 | Theeuwes | 417/48 X |
| 4,639,244 A | 1/1987 | Rizk et al. | 604/19 |
| 4,718,893 A | 1/1988 | Dorman et al. | 604/67 |
| 4,944,659 A | 7/1990 | Labbe et al. | 417/322 |
| 4,969,873 A | 11/1990 | Steinbach et al. | 604/93 |
| 5,041,107 A | 8/1991 | Heil | 604/891.1 |
| 5,277,774 A | 1/1994 | Schmidt et al. | 604/126 |
| 5,417,663 A | 5/1995 | Slettenmark | 604/126 |
| 5,443,461 A | 8/1995 | Atkinson et al. | 604/892.1 |
| 5,707,361 A | 1/1998 | Slettenmark | 604/131 |
| 5,836,935 A | 11/1998 | Ashton et al. | 604/891.1 |
| 5,869,078 A | 2/1999 | Baudino | 424/423 |
| 5,968,006 A | * 10/1999 | Hofmann | 604/20 |

* cited by examiner

*Primary Examiner*—William Wayner
(74) *Attorney, Agent, or Firm*—Francis L. Conte (57) ABSTRACT

An electrodiffusion pump includes a housing having an inlet, drug reservoir, and outlet. A diffusion membrane is disposed between the reservoir and outlet for diffusing the drug outwardly therethrough. Internal and external electrodes are disposed on opposite sides of the membrane. The electrodes are porous, and the external electrode is additionally perforate to expose a portion of the membrane at the outlet. The electrodes are electrically powered for driving drug ions through the membrane under electrophoresis to complement diffusion thereof.

22 Claims, 6 Drawing Sheets

PERFORATE ELECTRODIFFUSION PUMP

BACKGROUND OF THE INVENTION

The present invention relates generally to medicinal drug pumps, and, more specifically, to implantable molecular drug pumps.

U.S. Pat. No. 4,639,244-Rizk et al. discloses one type of electrodiffusion molecular pump for dispensing over time a suitable drug, such as insulin, when implanted in a patient. The pump has no moving parts and includes a selectively permeable diffusion membrane which permits controlled dispensing of drug molecules from an internal reservoir of the pump by diffusion through specifically sized pores in the membrane. Diffusion is a conventional process in which high concentration of molecules in a fluid will migrate to areas of low concentration. The pore size of the membrane is selected for passing the desired molecules, such as insulin, through the membrane at a controlled rate.

However, the drug diffusion rate is substantially fixed, and it is desired to vary the drug rate as required by the needs of the patient in which the pump is implanted. Accordingly, the pump further includes a pair of carbon mesh electrodes disposed on opposite sides of the diffusion membrane which are suitably electrically powered to effect electrophoresis. In this way, one electrode becomes a cathode, and the other electrode becomes an anode, and ionic drug molecules, such as negatively charged insulin, may be additionally driven through the membrane by the electrical field created between the electrodes.

By charging the electrode external of the diffusion membrane positive, and the electrode inside the pump reservoir on the opposite side of the membrane negative, the negative ions, or ionic molecules, may be electrically driven through the membrane with an increased delivery rate over that available solely for diffusion. Alternatively, the external electrode may be charged negative and the internal electrode may be charged positive for retarding diffusion through the membrane to decrease the delivery rate of the drug molecules.

In this way, the drug pump is configured for delivering the drug under diffusion at a substantially constant rate, which may be selectively increased or decreased by powering the electrodes for effecting electrophoresis, with the combination thereof being referred to as electrodiffusion.

Since it is desired to implant the pump in a human or animal patient for long periods, the pump itself should be relatively small and durable, and require little power to operate. However, these different objectives typically require compromises in the design of the pump.

For example, since the electrodes cover both sides of the diffusion membrane, they too must also be porous to permit dispensing of the drug outwardly therethrough. The electrode pores may be provided between the electrically conductive fibers forming the woven electrode mesh. The mesh should be woven tightly with fine fibers for maximizing the surface area of the electrode from which the electrical field is generated. Maximizing the surface area correspondingly decreases the power requirements for generating the electrical field during operation with maximum strength for effecting the electrophoresis migration of the drug ions.

In the above identified patent, the electrodes are formed by crossing small carbon fibers of about 1–10 microns in thickness in a tight mesh. However, testing conducted in recent developments suggests performance inefficiency during electrophoresis due to such mesh configuration.

Furthermore, the diffusion membrane is about 100–200 microns thick with minute micron-size pores therein, and is delicate and fragile. Accordingly, the repeated refilling of the drug reservoir in the pump can substantially shorten the useful life of the membrane when subjected to elevated differential pressure thereacross.

Accordingly, it is desired to provide an electrodiffusion ionic drug pump having an improved configuration for increasing durability and electrophoresis performance thereof.

BRIEF SUMMARY OF THE INVENTION

An electrodiffusion pump includes a housing having an inlet, drug reservoir, and outlet. A diffusion membrane is disposed between the reservoir and outlet for diffusing the drug outwardly therethrough. Internal and external electrodes are disposed on opposite sides of the membrane. The electrodes are porous, and the external electrode is additionally perforate to expose a portion of the membrane at the outlet. The electrodes are electrically powered for driving drug ions through the membrane under electrophoresis to complement diffusion thereof.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
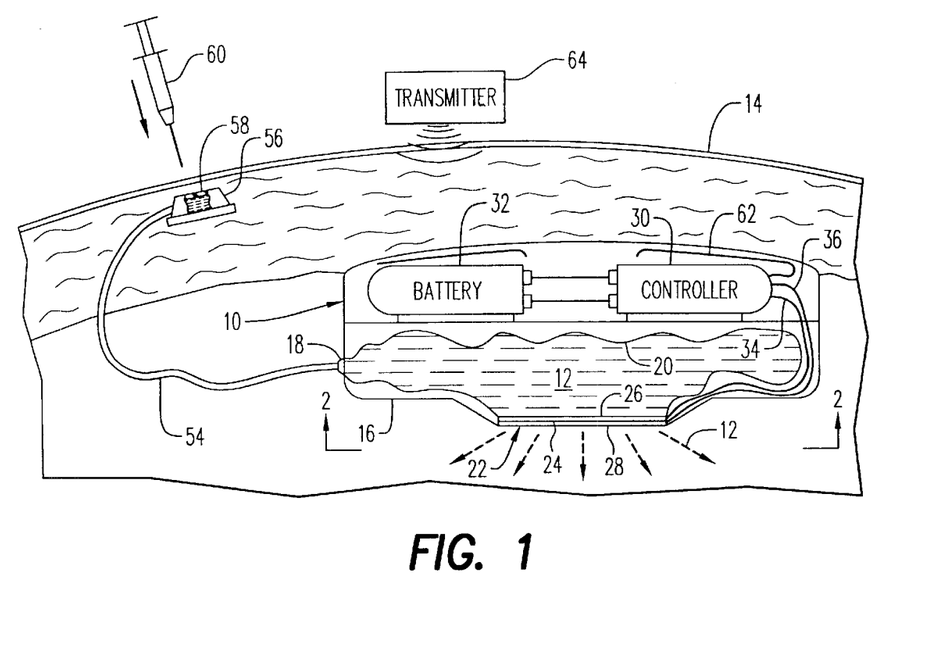
FIG. 1 is a schematic view of an electrodiffusion pump implanted below the skin of a patient in accordance with an exemplary embodiment of the present invention.

Illustrated schematically in FIG. 1 is an electrodiffusion pump 10 in accordance with one embodiment of the present invention for selectively dispensing an ionic drug 12 in a human or animal patient. The pump is preferably fully implanted under the skin 14 of the patient at any suitable location, such as partially within the peritoneum cavity.

The ionic drug 12 may have any conventional form as required for any medical use and may include, for example, insulin, peptide hormones, blood thinners, neurotrophics, antibiotics, analgesics, immunosuppressive agents, and pharmaceutical materials modified to carry an electrical charge. The drug molecules or ions may be negatively or positively charged, and are typically found in a suitable liquid solution. For example, commercially available insulin has negative ions or molecules at body temperature and is conventionally used for treating diabetes, typically by direct injection with a hypodermic syringe through the skin of a patient.

The ionic pump 10 illustrated in FIG. 1 may be implanted in the patient for continuously dispensing insulin to the patient with a variable rate as further described hereinbelow.

The pump includes a suitable housing 16 which is hermetically sealed and formed of a suitable inert material, such as titanium, for being implanted in the patient without adverse reaction.

The housing includes an inlet 18 in the form of one aperture through the wall thereof, an internal reservoir 20 for storing the liquid drug 12 therein, and an outlet 22 in the form of another aperture through the housing wall for dispensing or discharging the drug therefrom directly into the patient. The inlet and outlet are suitably joined to the reservoir in any convenient location for permitting refilling thereof after the drug is dispensed through the outlet.

Figure 2:
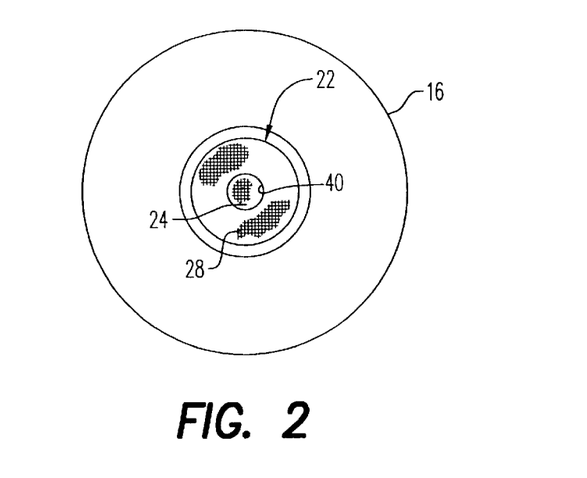
FIG. 2 is a plan view of the bottom of the pump illustrated in FIG. 1 and taken along line 2—2 for illustrating a drug outlet thereof exposed inside the patient.

As shown in plan view in FIG. 2, the outlet 22 is preferably disposed centrally at the bottom of the housing 16 and is circular in configuration. An enlarged cross section of the housing outlet 22 is illustrated in more detail in FIG. 3.

Figure 3:
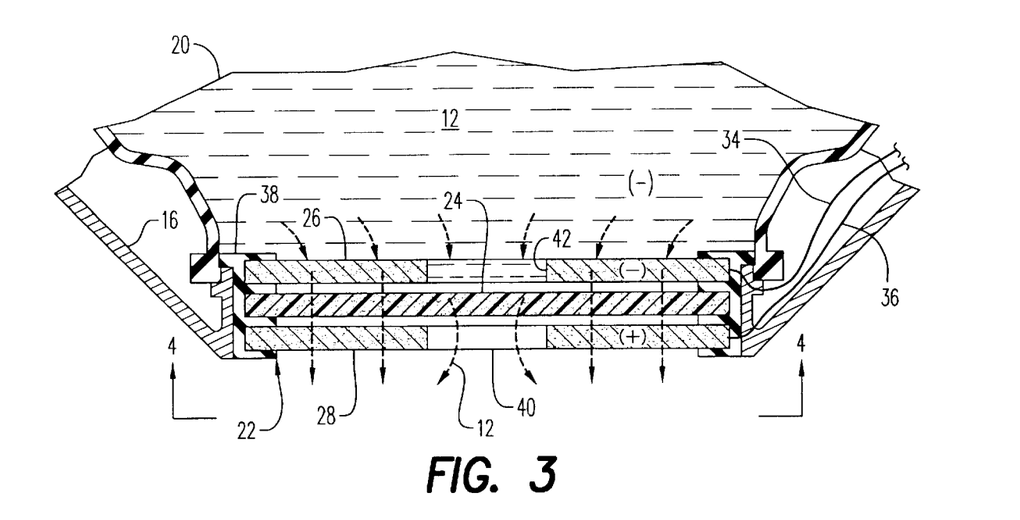
FIG. 3 is an enlarged, elevational sectional view through the outlet of the pump illustrated in FIG. 1, including a diffusion membrane sandwiched between a pair of internal and external electrodes in accordance with an exemplary embodiment of the present invention.

As shown in FIG. 3, a selectively permeable diffusion membrane 24 is disposed in flow communication between the discharge end of the reservoir 20 and the housing outlet 22 for diffusing the drug 12 outwardly therethrough. The membrane 24 extends across the circular housing outlet 22 and is suitably mounted around its circular perimeter to block the outlet and permit dispensing of the drug by diffusion through the membrane.

The diffusion membrane 24 includes minute pores specifically sized to permit molecules of the specific ionic drug 12 to pass therethrough by diffusion from the high concentration of the ionic drug in the liquid contained in the reservoir to the corresponding lower concentration found outside the pump outlet 22 in the immediate vicinity of the patient's body. The pump outlet is typically disposed in contact with normal bodily fluids inside the patient in which the ionic drug is infused by diffusion through the permeable membrane.

The diffusion membrane may have any conventional form and composition and may include, for example, cellulose esters, nylon polyvinylidene fluoride, polytetrafluoroethylene (PTFE), cellulose nitrate and acetate and mixtures thereof. The membrane may be about 100–200 microns thick, with pore sizes from about 0.025 microns to about 8 microns as desired for diffusion of the specific ionic molecules desired.

Commercially available diffusion membranes which may be used are sold under the tradenames MF, Celotate, Durapore, Mitex, and Fluoropore available from the Millipore Company of Bedford, Mass.

When the reservoir contains active drug, the concentration of drug inside the reservoir is significantly higher than the concentration of drug outside the reservoir. The drug will then diffuse through the selectively permeable membrane into the patient as a result of the concentration gradient across the membrane. The rate of diffusion is a function of the concentration gradient, the pore size of the membrane, and the mobility of the drug molecules which may be selected in a conventional manner.

Since the diffusion rate is a fixed rate, varying the rate of delivery of the drug is obtained in accordance with the present invention under the action of electrophoresis. Electrophoresis is effected by introducing a pair of electrodes 26,28 on opposite sides of the membrane 24, as initially illustrated in FIG. 1, and powering those electrodes to create an electrical field for driving the drug ions therebetween.

As shown in more detail in FIG. 3, a first or internal electrode 26 is disposed inside the reservoir 20 at its discharge end at the outlet of the housing along the internal side of the membrane 24. A second or external electrode 28 is disposed outside the reservoir in the housing outlet along an external side of the membrane.

Referring again to FIG. 1, suitable means in the form of electrical controller 30 and power supply, such as a battery 32, are operatively joined to the two electrodes 26,28 by corresponding electrical leads 34,36. The controller 30 may have any conventional form such as an electronic circuit specifically configured for operating the pump, or a digitally programmable microprocessor as desired. The controller 30 is suitably configured for powering the electrodes 26,28 as cathode and anode as desired for additionally driving the ionic drug 12 through the membrane under electrophoresis.

As shown in cross section in FIG. 3, the internal and external electrodes 26,28 are porous for channeling the drug therethrough with diffusion occurring through the membrane 24 sandwiched therebetween for discharge from the pump outlet 22. The electrodes 26,28 are porous also for maximizing the available surface area thereof in which an electrical field may be generated between the two electrodes with maximum strength and minimum power requirements for prolonging the useful life of the battery during operation.

The pores of the two electrodes should be as small as possible for maximizing surface area, while also being sufficiently large for permitting passage of the ionic drug therethrough without obstruction. Accordingly, the pore size of the electrodes should be preferably no less than the pore size of the diffusion membrane, and is preferably greater to avoid flow obstruction.

In this way, when the electrodes are powered for effecting electrophoresis, the maximum electrical field with minimum power may be obtained for electrically driving the drug ions between the electrodes and through the membrane for either increasing or decreasing the delivery rate therethrough.

For the example of insulin having negative ions, the external electrode 28 is powered as a positive anode and the internal electrode 26 is powered as a negative cathode so that the negative insulin ions are driven from the internal electrode and through the membrane to the external electrode by the electrical field generated therebetween. In this active mode of operation, electrophoresis increases the rate of ion delivery through the membrane 24 for providing more drug to the patient.

Figure 4:
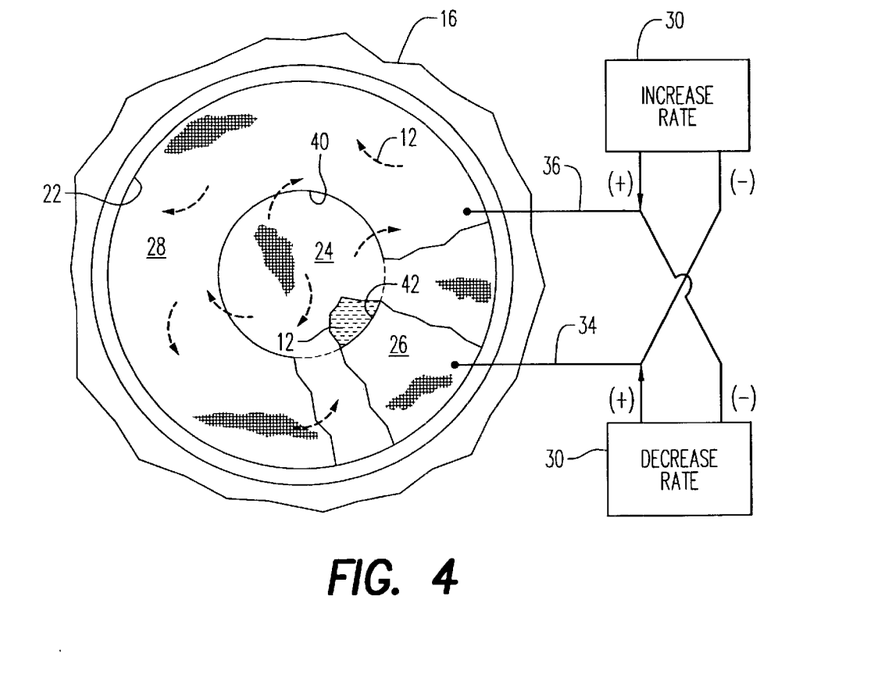
FIG. 4 is a partly sectional, schematic view of the pump outlet illustrated in FIG. 3 and, taken along line 4—4 for illustrating diffusion and complementing electrophoresis with a variable rate.

This increased rate of drug delivery is illustrated schematically in FIG. 4 with the controller 30 being configured for powering the internal and external electrodes as cathode and anode, respectively. Correspondingly, in order to decrease or retard the rate of drug delivery through the membrane, the controller 30 may also be configured to invert the polarity of the internal and external electrodes 26,28 to form anode and cathode, respectively. In this way, the electrical field generated by the cathode external electrode 28 and the anode internal electrode 26 opposes the outward migration of the negative drug ions through the membrane.

In the example of treating diabetes in the patient by the delivery of insulin from the pump, a base therapeutic rate of medication is preferably delivered continuously through the membrane. This basal delivery rate should be preferably higher than the passive diffusion rate of the membrane itself so that the rate may be readily decreased in the event that the patient is receiving too much drug in any interval of time.

Accordingly, for the basal delivery of the drug, both electrodes are powered at a relatively low level for effecting a correspondingly low level of electrophoresis which in combination with the passive diffusion rate of the drug through the membrane creates the desired basal rate of delivery. The electrodes may be powered by a continuous D.C. voltage, or may be suitably modulated in voltage magnitude as desired to effect the desired electrophoresis supplementing basal rate of delivery.

When a higher dose of medication is desired in the patient, the controller 30 is configured for providing a higher voltage to the electrodes to increase the electrical field therebetween, and correspondingly increase the electrophoresis action. In this way, a bolus or higher dose of medication may be dispensed from the pump when desired by the combination of diffusion and electrophoresis.

Accordingly, the rate of drug delivery through the membrane 24 may be increased selectively by electrophoresis with a corresponding amount of electrical field generated between the electrodes. And, the drug delivery rate may be decreased or inhibited by reversing the polarity of the electrodes for opposing the outward travel of the ionic drug through the membrane when desired.

As illustrated in FIGS. 3 and 4, the effect of electrophoresis may be maximized in accordance with a preferred embodiment of the present invention by using an external electrode 28 which is not only porous, but is further perforate to expose a corresponding portion of the diffusion membrane 24 at the pump outlet 22 for providing a direct and unobstructed flowpath for the drug into the patient.

As initially shown in FIG. 3, both electrodes 26,28 are preferably in the form of thin mesh sheets having corresponding pores therein on opposite sides of the porous membrane 24. The electrodes are mounted around their perimeters in a suitable electrical insulator 38 so that they extend substantially parallel to the membrane, and laterally or diametrically across the respective internal and external sides thereof.

The external electrode 28 is perforate to include at least one external aperture 40 extending therethrough and facing outwardly from the underlying membrane 24 to expose the corresponding portion thereof. The external aperture 40 may have any suitable configuration and size and is substantially larger than the surrounding micron-size smaller mesh pores in the remainder of the external electrode.

In this way, the porous electrodes may be configured for maximizing their surface area for effecting electrophoresis, yet the external aperture 40 is provided to ensure a direct flowpath from the membrane and through the external electrode locally bypassing the pores thereof.

In the preferred embodiment illustrated in FIG. 3, the porous internal electrode 26 is correspondingly perforate to include an internal aperture 42 extending therethrough and facing inwardly into the reservoir from the membrane to match the configuration of the external electrode. The internal aperture 42 is substantially larger than the micron-size mesh pores of the internal electrode and provides a direct flowpath from the reservoir to. the membrane 24 without obstruction by the surrounding portion of the internal electrode.

In the exemplary embodiment illustrated in FIGS. 3 and 4, each of the internal and external electrodes 26,28 preferably includes a single central aperture 42,40 therein aligned with each other on opposite sides of the membrane. This embodiment was built and tested and effected significant electrophoresis to not only increase delivery rate through the membrane under forward polarity, but also significantly retarded delivery rate under reverse polarity.

In the preferred embodiment tested, the internal and external electrodes 26,28 were formed of a gold mesh commercially available from the Buckbee-Mears company of St. Paul, Minn. The gold mesh electrodes had a outer diameter of about 19 mm, a central aperture of about 6 mm, and a pore or mesh size of about 0.25 to 0.51 microns (or 10–20 microinch).

The porous electrodes may also be formed of any suitable material including silver/silver chloride, carbon, carbon mesh, and platinum, for example. The electrodes should be chemically inert for implantation in a patient and should have suitable electrical conduction capability, with minimum electrical resistance for maximizing the electrical field generated between the two electrodes.

Since the internal and external electrodes cover both sides of the membrane disposed therebetween as illustrated in FIG. 3, the corresponding pores thereof permit diffusion of the ionic drug therethrough as well as migration of the ionic drug under the electrical field generated in electrophoresis. The introduction of the relatively large apertures 40,42 provides an additional unobstructed flowpath directly to and from the porous membrane 24 for diffusion of the ionic drug, as well as for electrophoresis to avoid accumulation or adhesion of the drug within the pores of the external electrode.

Figure 5:
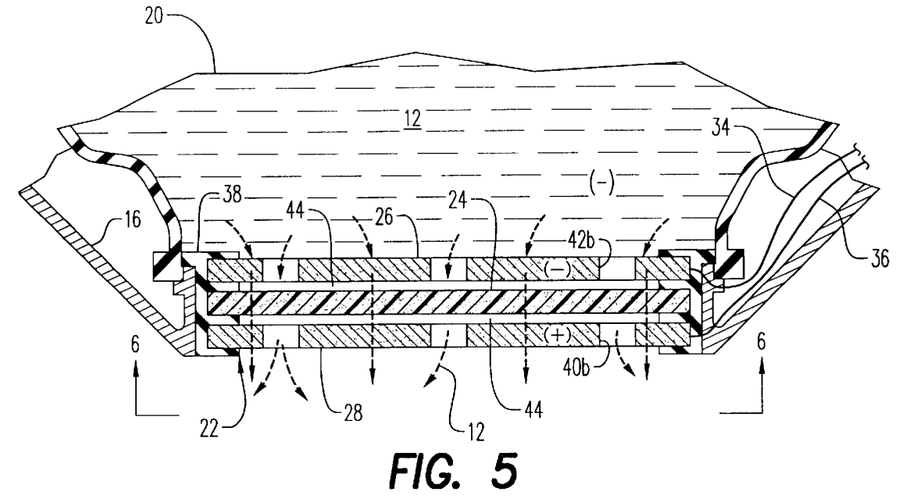
FIG. 5 is an enlarged elevational sectional view, like FIG. 3, of the pump outlet in accordance with another embodiment of the present invention having a plurality of apertures in the cooperating electrodes.
Figure 6:
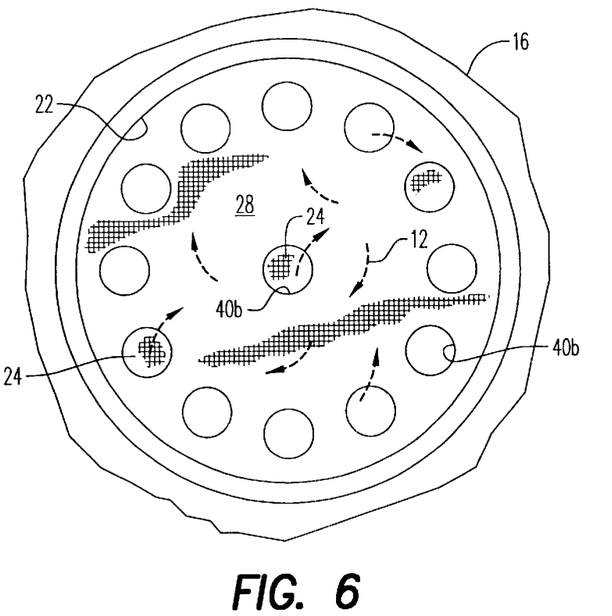
FIG. 6 is a plan view of the pump outlet illustrated in FIG. 5 and taken along line 6—6.

FIGS. 5 and 6 illustrate an alternate embodiment of the invention including respective pluralities of external and internal apertures 40b,42b in the corresponding electrodes 28,26 instead of a central single aperture therein.

Since the pump outlet 22 is circular, the external apertures 40b are arranged in a ring inside the perimeter of the pump outlet with a suitable circumferential spacing therebetween. And, a central aperture is also used in this embodiment. The several external apertures 40b are preferably equally sized in diameter of about one (1) mm, for example, and are substantially larger than the micron-size pores of the electrodes. The collective area of the external apertures illustrated in FIG. 6 may be equal to the area of the single larger central aperture 40 in the FIG. 4 embodiment.

In the FIG. 6 embodiment, the multiple apertures are spaced part from each other to provide multiple unobstructed flowpaths to and from the underlying diffusion membrane 24 for enhancing electrophoresis of the drug ions without accumulation in the small pores of the external electrode. During electrophoresis, the drug ions can locally bypass the electrode pores for unrestrained flow through the multiple apertures.

In the preferred embodiment illustrated in FIG. 5, the internal electrode 26 matches the configuration of the external electrode and includes an equal number of internal apertures 42b having the same size as the external apertures 40b and aligned therewith for providing direct flowpaths to the respective portions of the diffusion membrane 24 disposed therebetween. In this way, diffusion of the ionic drug occurs through the opposite electrodes and intervening membrane, with electrophoresis also being effected therebetween with discrete flowpaths provided therefor by the aligned apertures. Electrophoretic migration of the ions may thusly bypass the electrode pores for enhanced drug delivery. In the exemplary embodiment illustrated in FIG. 5, the external electrode 28 is mounted in the insulator 38 closely adjacent to the external surface of the membrane 24 to effect a small gap 44 therebetween which is empty of solid material for receiving the drug upon passing through the pores of the membrane.

Similarly, the internal electrode 26 is suitably mounted in the insulator 38 closely adjacent to the inner surface of the membrane and spaced therefrom to effect another gap 44 therebetween which is also empty of solid material for receiving the liquid drug in the reservoir. In this way, the entire exposed internal surface of the membrane 24 is in contact with the liquid drug in the reservoir for permitting diffusion of the drug over the maximum available surface area of the membrane. Furthermore, the internal and external electrodes cover the opposite sides of the membrane for effecting electrophoresis over the full exposed surface area thereof.

Figure 7:
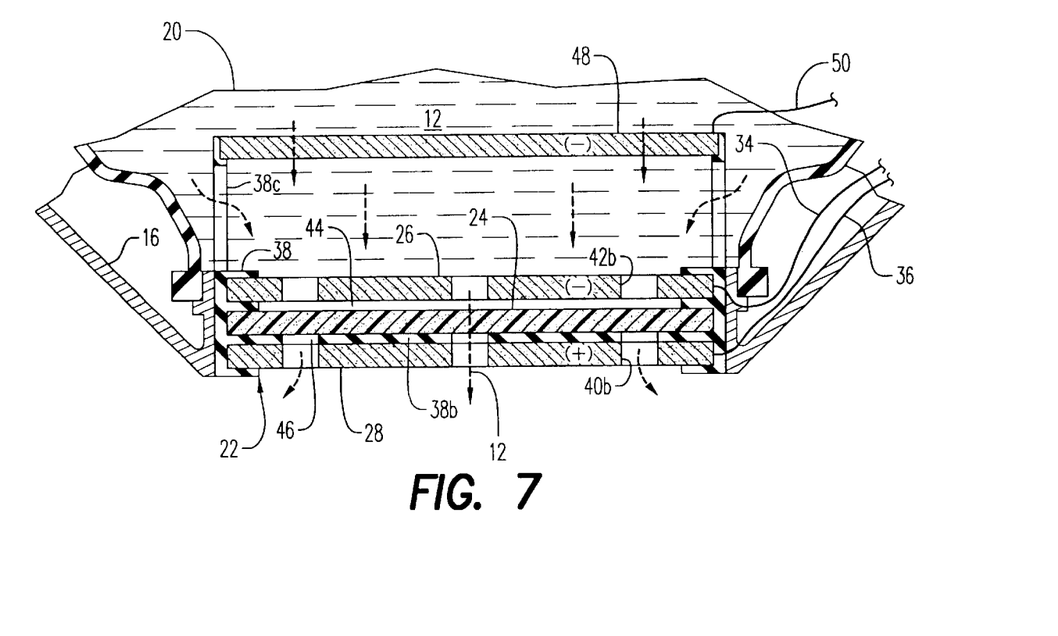
FIG. 7 is an enlarged elevational sectional view, like FIG. 3, of the pump outlet in accordance with another embodiment of the present invention including two internal electrodes therein.

Illustrated in FIG. 7 is yet another embodiment of the present invention wherein the external electrode 28 is directly laminated in abutting contact to the outer surface of the diffusion membrane 24 by a sheet or disk portion 38b of the electrical insulator 38 supporting the perimeter of the electrode. The insulator disk 38b is perforate and includes respective apertures 46 matching the external apertures 40b preferably in both size and position and aligned therewith. However, the insulator disk 38b is preferably otherwise solid without pores between the apertures 46 thereof.

Preferably, the apertures 40b and 46 in the external electrode and insulator disk have equal size and are aligned for providing discrete, unobstructed flowpaths from respective portions of the external surface of the diffusion membrane 24. In this way, the solid insulator disk 38b obstructs the back side of the external electrode 28 to prevent or inhibit the accumulation of the ionic drug thereat, with the ionic drug instead being channeled through the aligned apertures in the external electrode.

Figure 8:
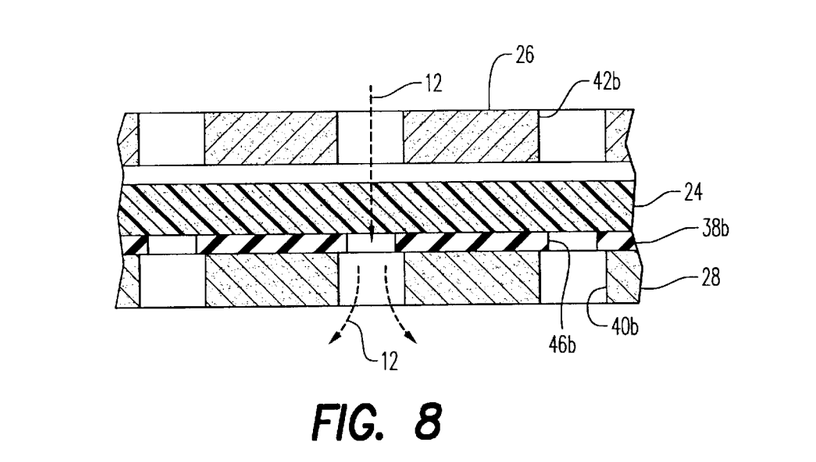
FIG. 8 is an enlarged sectional view of a portion of the pump outlet illustrated in FIG. 7 in accordance with another embodiment thereof.

FIG. 8 illustrates yet another embodiment of the invention wherein the solid insulator disk 38b shown in FIG. 7 includes apertures 46b which are correspondingly smaller than the external apertures 40b of the external electrode 28 and aligned therewith. In this way, a step is defined between the smaller insulator apertures 46b and the larger external apertures 40b for further restraining accumulation of the ionic drug during electrophoresis within the pores of the external electrode 28.

FIG. 7 also illustrates yet another embodiment of the present invention including another internal or remote porous electrode 48 spaced inwardly from the internal electrode 26 and the diffusion membrane 24 inside the reservoir. The remote electrode 48 is electrically joined to the controller 30 illustrated in FIG. 1 by a corresponding electrical lead 50.

The remote electrode 48 is similar in size to the pump outlet 22 and the internal electrode 26 therein, and is suspended or supported inside the reservoir by a plurality of circumferentially spaced apart, vertically extending standoff ribs 38c which are electrically insulating extensions of the insulator 38. In this way, the liquid drug within the reservoir 20 is permitted to flow without obstruction between the remote electrode 48 and the internal electrode 26.

The remote electrode 48 may be configured like the internal electrode 26, without the need for apertures therein, and is correspondingly porous for maximizing the available surface area thereof for effecting an electrical field with minimum power requirements. Both the remote electrode 48 and the internal electrode 26 are joined to the controller for carrying the same polarity which is opposite to that of the external electrode 28.

The voltage applied to the two internal electrodes may be suitably different in magnitude from each other for promoting electrophoresis. In this way, the remote electrode 48 may drive the ionic molecules toward the internal electrode 26, which molecules are further driven by the internal electrode through the membrane to the external electrode when the electrodes are powered for electrophoresis.

In an alternate embodiment, the internal electrode closest to the membrane 24 may be eliminated, and the remote internal electrode 48 may be used alone in combination with the external electrode 28.

Figure 9:
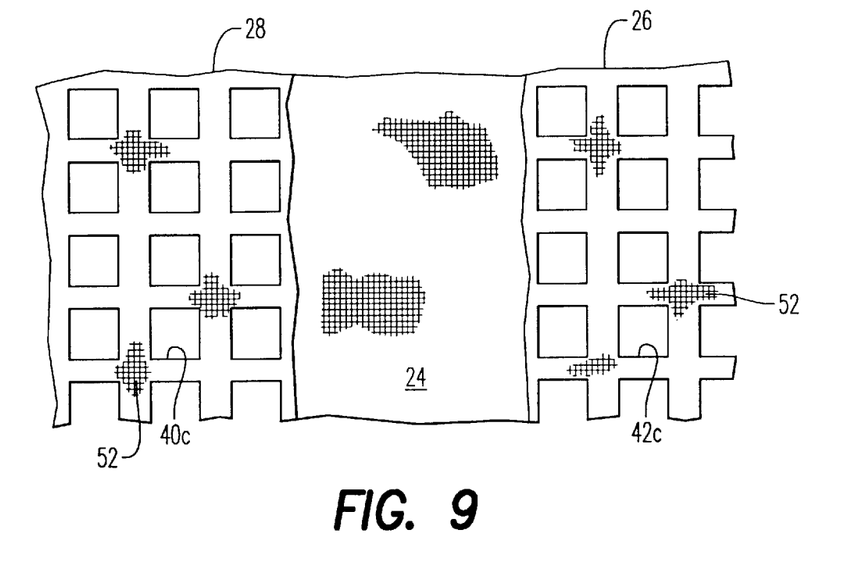
FIG. 9 is a partly sectional view plan view of a portion of the pump outlet illustrated in FIG. 1 having electrode grid apertures in accordance with another embodiment of the present invention.

In the exemplary embodiment illustrated in FIGS. 2–8, the apertures in the electrodes are preferably circular. FIG. 9 illustrates yet another embodiment of the invention wherein the internal electrode 26 includes rectangular or square apertures 42c, and the external electrode 28 includes corresponding rectangular or square apertures 40c. The apertures in the two electrodes are arranged in a rectangular grid between surrounding border portions of the electrodes containing the pores therein.

A particular advantage of the rectangular apertures illustrated in FIG. 9 is that the sheet electrodes 26,28 may be woven from electrically conducting fibers 52 crossing transversely or perpendicularly to each other in a woven fabric to define the small pores between the intersecting fibers, as well as the large rectangular apertures therein.

In the preferred embodiment illustrated in FIG. 1, the reservoir 20 is in the form of a flexible sack or bag with a flexible boundary wall disposed inside the housing 16. The flexible reservoir increases in volume as it is initially filled with the liquid drug, and elastically accommodates volume changes without unduly deforming or pressurizing the fragile membrane 24. Since the membrane is quite thin, avoiding differential pressure thereacross is desired for preventing damage thereto which would shorten the useful life of the membrane when implanted in the patient.

As shown in FIG. 1, the housing 16 may be implanted at any convenient location inside a patient, and further includes a flexible catheter or tube 54 joined in flow communication between the housing inlet 18 and a remote inlet 56 implanted at a convenient location directly under the skin 14. The remote inlet includes a resealable elastomeric plug 58, which may be made of silicon for example, for receiving a hypodermic syringe or needle 60 for delivering the liquid drug into the reservoir. The needle is inserted through the skin and into the remote inlet plug, and the liquid drug is injected into the remote inlet for flow through the tube 54 to replenish the drug supply inside the reservoir 20.

Since the drug itself is carried in a suitable liquid carrier, infusion into the body of the drug leaves behind a carrier liquid inside the reservoir. Accordingly, in order to replenish the liquid drug in the pump, a syringe is first used for removing the depleted liquid carrier from the pump, and then re-injecting into the pump a replacement supply of the liquid drug. Since the reservoir 20 is flexible, withdrawal or replacement of the liquid therein introduces little, if any, differential pressure across the fragile membrane 24 during drug re-supply.

The pump illustrated in the preferred embodiment of FIG. 1 preferably also includes a suitable internal antenna 62 operatively joined to the controller 30 which cooperates with a suitable transmitter 64 positioned outside the skin 14. In this way, the controller 30 may be programmed or adjusted as desired by radio communication from outside the patient. The controller may be programmed to cycle on and off as desired for controlling the electrophoresis effected by the powered electrodes 26,28 as required for infusion of the specific drug being dispensed.

Figure 10:
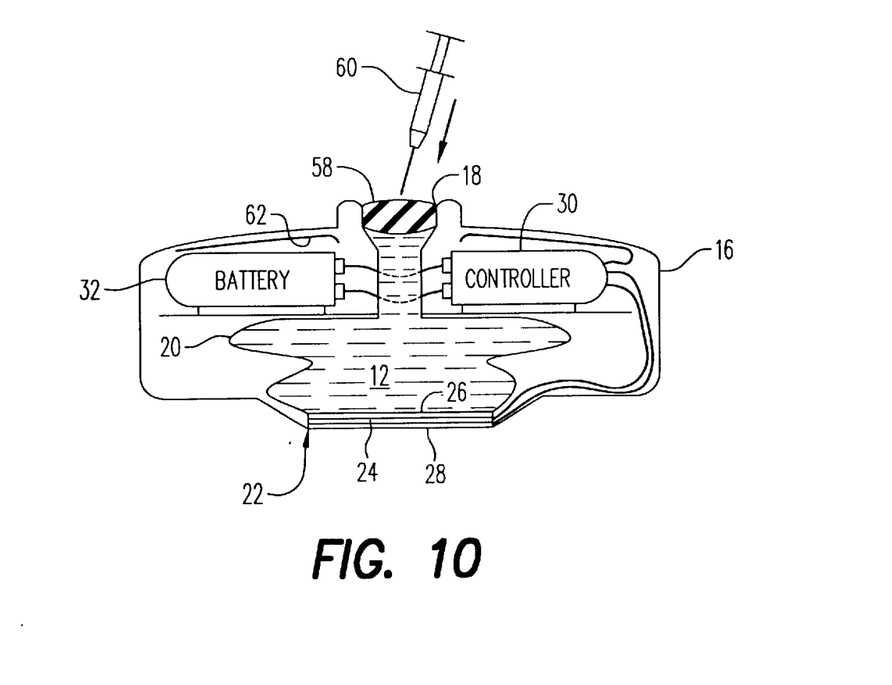
FIG. 10 is an elevational sectional view of the pump illustrated in FIG. 1 in accordance with another embodiment of the present invention having a resealable inlet for receiving a hypodermic needle to refill the drug reservoir.

FIG. 10 illustrates a variation of the pump shown in FIG. 1 without the remote inlet 56 or tube 54. In this embodiment, the housing inlet 18 is provided in the top thereof and includes the elastomeric plug 58 exposed therein. The pump may be implanted directly below the skin so that the hypodermic needle 60 may be inserted through the skin and into the plug 58 to initially fill the flexible reservoir 20, as well as resupplying the reservoir when desired.

Figure 11:
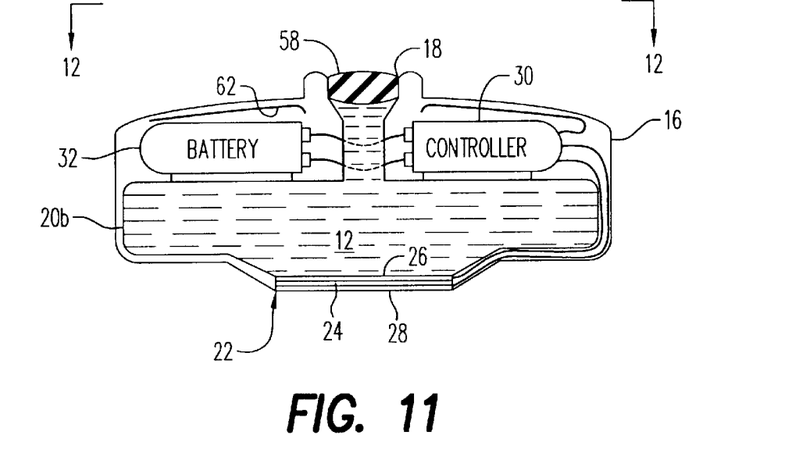
FIG. 11 is an elevational sectional view of the pump illustrated in FIG. 1 in accordance with another embodiment of the present invention having a rigid internal reservoir and a pair of resealable inlets joined thereto.
Figure 12:
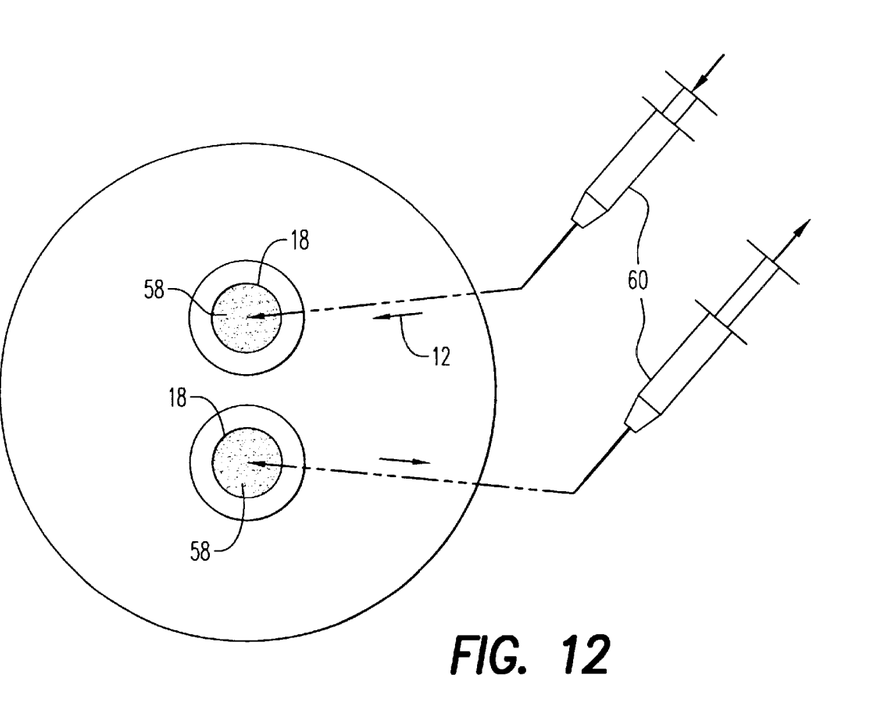
FIG. 12 is a plan view of the top of the drug pump illustrated in FIG. 11 and taken along line 12—12 to schematically illustrate refilling of the reservoir therein.

Illustrated in FIGS. 11 and 12 is yet another embodiment of the present invention wherein the reservoir, designated 20b, is in the form of a rigid plenum having a rigid boundary wall disposed inside the housing 16. The reservoir thusly has a fixed volume for containing the liquid drug 12 therein.

Since the reservoir is rigid, the housing 16 preferably includes two of the inlets 18 with corresponding resealable elastomeric plugs 58 therein. Both inlets are joined in flow communication with the common reservoir.

As shown in FIG. 12, two syringes 60 are used simultaneously in respective ones of the inlets 18 for simultaneously injecting the liquid drug 12 into the reservoir while withdrawing either air or depleted liquid carrier from the reservoir for reducing or preventing differential pressures across the fragile membrane 24 during replenishment. By simultaneously removing a substantially equal amount of liquid from the reservoir as the replenishment drug is injected, the pressure buildup in the reservoir is minimized for protecting the membrane from damage.

The various embodiments of the electrodiffusion ionic drug pump disclosed above have drug outlets configured for improved infusion of the ionic drug continuously by diffusion and selectively by electrophoresis to either accelerate or retard the total infusion rate of the drug. The introduction of the relatively large apertures in the external electrode in additional to the relatively small pores therein promotes both diffusion as well as enhanced electrophoresis for reducing the accumulation of drug ions within the pores of the external electrode. The external apertures are selectively introduced for maintaining an effective electrical field strength between the electrodes while promoting electrophoresis through the apertures which bypass the electrode pores.

The electrode apertures may have any suitable form, size, and pattern in the respective electrodes for maximizing the effect of electrophoresis while minimizing the amount of electrical power required to create the driving electrical field.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which we claim:

1. An electrodiffusion pump for dispensing an ionic drug comprising:
   a housing having an inlet for receiving said drug, a reservoir for storing said drug, and an outlet for discharging said drug;
   a diffusion membrane disposed in flow communication between said reservoir and outlet for diffusing said drug outwardly therethrough;
   an internal electrode disposed inside said reservoir along an internal side of said membrane;
   an external electrode disposed outside said reservoir along an external side of said membrane;
   said internal and external electrodes being porous for channeling said drug therethrough, and said external electrode further being perforate to expose a portion of said membrane at said outlet; and
   means for electrically powering said electrodes as cathode and anode for additionally driving said ionic drug through said membrane under electrophoresis.

2. A pump according to claim 1 wherein:
   said internal and external electrodes comprise mesh sheets disposed parallel to said membrane laterally across said internal and external sides thereof; and
   said external electrode is perforate to include an external aperture facing outwardly from said membrane to expose said portion thereof, and said aperture is surrounded by smaller pores.

3. A pump according to claim 2 wherein said internal electrode is perforate to include an internal aperture facing inwardly from said membrane to match said external electrode.

4. A pump according to claim 3 wherein said internal and external electrodes each includes a single central aperture therein aligned with each other on opposite sides of said membrane.

5. A pump according to claim 3 wherein said internal and external electrodes each includes a plurality of apertures therein aligned with each other on opposite sides of said membrane.

6. A pump according to claim 5 wherein said outlet is circular, and said electrode apertures are arranged in a ring inside the perimeter of said outlet.

7. A pump according to claim 5 wherein said electrode apertures are rectangular and arranged in a rectangular grid.

8. A pump according to claim 7 wherein said internal and external electrodes include fibers crossing transversely to define said pores and rectangular apertures therebetween.

9. A pump according to claim 3 wherein said internal and external electrodes includes fibers crossing transversely to define said pores and apertures therebetween.

10. A pump according to claim 3 wherein said external electrode is spaced from said membrane to effect a gap therebetween.

11. A pump according to claim 3 wherein said external electrode is laminated to said membrane by an intervening electrical insulator being perforate to match said perforate external electrode.

12. A pump according to claim 11 wherein said insulator and external electrode have equal size apertures aligned therethrough.

13. A pump according to claim 11 wherein said insulator includes an aperture smaller than said aperture of said external electrode and aligned therewith.

14. A pump according to claim 11 wherein internal electrode is spaced from said membrane to effect a gap therebetween.

15. A pump according to claim 14 further comprising a remote electrode spaced inwardly from said internal electrode inside said reservoir, and electrically joined to said powering means to carry the same polarity as said internal electrode.

16. A pump according to claim 15 further comprising a plurality of ribs supporting said remote electrode above said internal electrode for permitting unobstructed flow of said drug therebetween inside said reservoir.

17. A pump according to claim 2 wherein said internal electrode is spaced inwardly from said membrane to effect a gap therebetween.

18. A pump according to claim 17 further comprising a plurality of ribs supporting said internal electrode above said membrane for permitting unobstructed flow of said drug therebetween inside said reservoir.

19. A pump according to claim 2 wherein said reservoir has a flexible boundary wall inside said housing for accommodating volume changes of said drug therein without pressurizing said membrane.

20. A pump according to claim 19 wherein said inlet includes an elastomeric plug for receiving a hypodermic needle 60 therethrough to fill said reservoir with said drug.

21. A pump according to claim 19 further comprising:
a tube joined in flow communication between said housing inlet and a remote inlet; and said remote inlet includes an elastomeric plug for receiving a hypodermic needle therethrough to deliver said drug to said reservoir through said tube.

22. A pump according to claim 2 wherein:
said reservoir has a rigid boundary wall inside said housing with a fixed volume for said drug; and said housing includes two of said inlets for simultaneously filling said reservoir with said drug through one inlet while removing a substantially equal amount of liquid from said reservoir through the other inlet.

* * * * *